US00PP36210P2

(12) United States Plant Patent
Lim

(10) Patent No.: US PP36,210 P2
(45) Date of Patent: Oct. 22, 2024

(54) FLORIBUNDA ROSE PLANT NAMED 'LIMtropica'

(50) Latin Name: *Rosa hybrida*
Varietal Denomination: LIMtropica

(71) Applicant: Altman Specialty Plants Inc., Vista, CA (US)

(72) Inventor: Peter Lim, Escondido, CA (US)

(73) Assignee: Altman Specialty Plants Inc, Vista, CA (US)

( * ) Notice: Subject to any disclaimer, the term of this patent is extended or adjusted under 35 U.S.C. 154(b) by 0 days.

(21) Appl. No.: 18/371,541

(22) Filed: Sep. 22, 2023

(51) Int. Cl.
*A01H 5/02* (2018.01)
*A01H 6/74* (2018.01)

(52) U.S. Cl.
USPC ..... Plt./150

(58) Field of Classification Search
USPC ..... Plt./102, 107, 108, 141, 150
See application file for complete search history.

*Primary Examiner* — Susan McCormick Ewoldt
*Assistant Examiner* — Zachariah Allan Kay
(74) *Attorney, Agent, or Firm* — Cassandra Bright

(57) ABSTRACT

A new and distinct cultivar of Floribunda Rose plant named 'LIMtropica' is disclosed, characterized by distinctive orange and pink flowers with a moderate tea rose fragrance. Plants are vigorous and can be grown on their own roots. Plants are compact, flower continuously and exhibit good resistance to blackspot diseases. The new variety is normally produced as an outdoor garden or container plant.

2 Drawing Sheets

Figure 1:
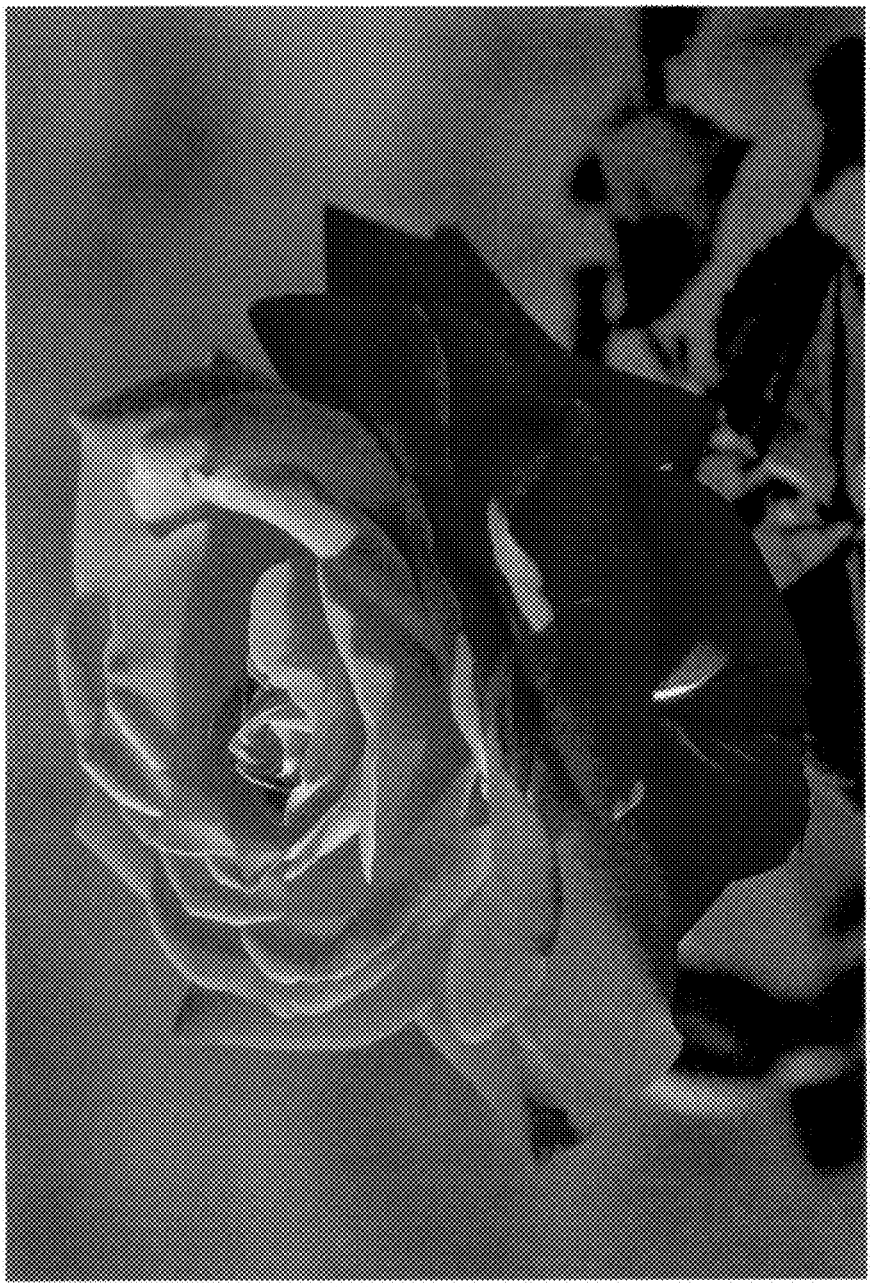

Latin name of the genus and species: *Rosa hybrida.*
Variety denomination: 'LIMtropica'.

BACKGROUND OF THE INVENTION

The new *Rosa* cultivar is a product of a planned breeding program conducted by the inventor. The objective of the breeding program was to produce vigorous new garden rose varieties with continuous blooming for ornamental commercial applications. The cross resulting in this new variety was made during June of 2011 in McMinnville, Oregon.

The seed parent is unnamed bicolor *Rosa* seedling. The pollen parent is the variety *Rosa* 'Knock Out', U.S. Plant Pat. No. 11,836. The new variety was selected Aug. 1, 2012 by the inventor in a group of seedlings resulting from the 2011 crossing, in a nursery in McMinnville, Oregon.

Asexual reproduction of the new cultivar has been performed by vegetative cuttings. This was first performed at a research greenhouse in Vista, California Aug. 15, 2012 and has shown that the unique features of this cultivar are stable and reproduced true to type in more than 5 successive generations.

SUMMARY OF THE INVENTION

The cultivar 'LIMtropica' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LIMtropica' These characteristics in combination distinguish 'LIMtropica' as a new and distinct *Rosa* cultivar:

1. Orange and pink colored flowers.
2. Vigorous compact habit.
3. Early, prolific, continuous blooming.

4. Dark glossy foliage resistant to black spot and powdery mildew disease.
5. Plants can be grown on their own roots; grafting is not required.

PARENT COMPARISONS

Plants of the new cultivar 'LIMtropica' are similar to plants of the seed parent, in most horticultural characteristics, however, plants of the new cultivar 'LIMtropica' differ in the following:

1. The new variety has flower with mixed orange and pink coloration, without a strong definition between the colors. The seed parent has a pink and white bi-color flower with a definition between the colors.

Plants of the new cultivar 'LIMTROPICA' are similar to plants of the pollen parent in most horticultural characteristics, however, plants of the new cultivar 'LIMTROPICA' differs in the following;

1. Flower color of the new variety are orange and pink, while flower color of the pollen parent is red.

COMMERCIAL COMPARISONS

Plants of the new cultivar 'LIMtropica' can be compared to the commercial variety *Rosa* 'MACtrum', U.S. Plant Pat. No. 4,297. These varieties are similar in most horticultural characteristics, however 'LIMtropica' differs in the following:

1. Flower color of the new variety is orange and pink, while the flower color of this comparator is red-orange.
2. Plant habit of the new variety is compact, while the plant habit of this comparator is spreading.

Plants of the new cultivar 'LIMtropica' can also be compared to the commercial variety *Rosa* 'WEKlovapkemu', U.S. Plant Pat. No. 32,109. These varieties are similar in most horticultural characteristics, however 'LIMtropica' differs in the following:

1. Flower color of the new variety are orange and pink, while flower color of this comparator is orange and yellow.

BRIEF DESCRIPTION OF THE PHOTOGRAPHS

The accompanying photograph in FIG. 1 illustrates in full color a close up of an individual flower of 'LIMtropica' on a plant of approximately 2-years old.

Figure 2:
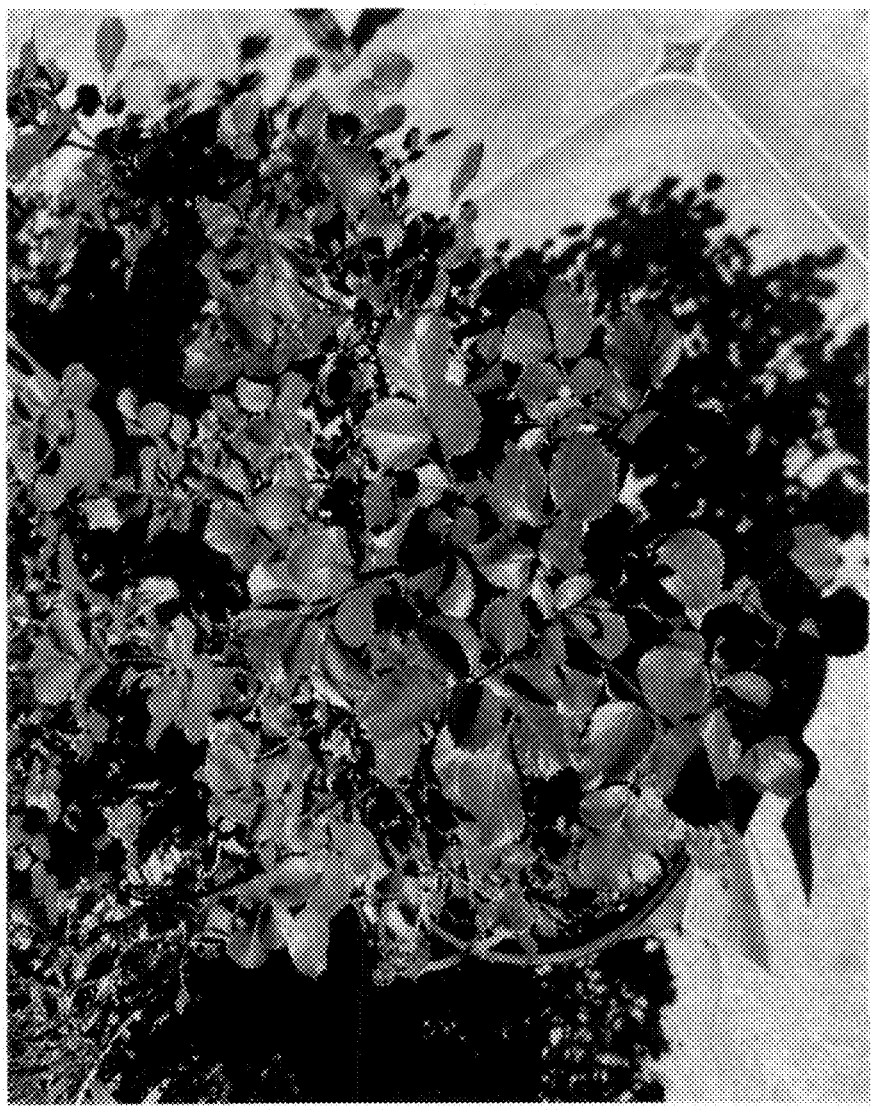

FIG. 2 is a plant of 'LIMtropica', photographed in April in Southern California, showing plant form and foliage at approximately 2.5 years.

The photographs were taken using conventional techniques and although colors may appear different from actual colors due to light reflectance it is as accurate as possible by conventional photographic techniques

DETAILED BOTANICAL DESCRIPTION

In the following description, color references are made to The Royal Horticultural Society Colour Chart 2007 except where general terms of ordinary dictionary significance are used. The following observations and measurements describe 'LIMtropica' plants grown outdoors, in Palm Desert, California. The growing temperature ranged from approximately 10° C. to 38° C. during the day and from approximately 5° C. to 22° C. during the night. Measurements were taken in September. General light conditions were very bright, normal sunlight. Measurements and numerical values represent averages of typical plant types.

Botanical classification: *Rosa* 'LIMtropica'.

Market classification: Floribunda rose.

PROPAGATION

Time to initiate roots: About 15 days at approximately 20° C.

Time to produce a rooted cutting: About 35 days at approximately 20° C.

PLANT

Age of plant described: Approximately 1.5 years.

Growth habit: Compact.

Container size: 2 gallon.

Height: 35 cm.

Plant spread: 45 cm.

Rootstock: Own root.

Growth rate: Moderate.

Branching characteristics: Sympodial branching.

Length of primary lateral branches: Average range 10 to 15 cm.

Diameter of lateral branches: Approximately 5 mm to 7 mm.

Quantity of branches: 6 to 10 main branches.

Internode length: Average range 2.2 cm to 3.8 cm.

Branches-young wood:

*Diameter.*—Approximately 4 mm.

*Texture.*—Glabrous. No prickles or very sparse minute prickles.

*Color.*—Near RHS Green 143C.

Branches-old wood:

*Diameter.*—Approximately 7 mm.

*Color.*—Near RHS Grey-Brown 199C lightly streaked Green 138B.

*Texture.*—Glabrous. Almost no prickles.

*Prickles.*—

*Approximate density/quantity of prickles.*—Young growth: No prickles or very sparse. Approximately 3 mm in diameter at base and 2 mm to 3 mm long. Colored near RHS Green 143C lightly flushed Greyed-Red 178D. Soft, not sharp.

*Mature growth: Sparse to none. Approximately* 3 mm in diameter at base and 3 mm long. Colored near RHS Greyed-Red 178B. Pointed.

FOLIAGE

Leaf:

*Arrangement.*—Alternate and compound.

*Quantity.*—Average 10 to 16 per main branch.

*Internode.*—Average range 1 cm.

*Average length.*—5.5 cm to 6.5 cm.

*Average width.*—4.5 cm to 5 cm.

Rachis:

*Average length.*—2 cm.

*Average diameter.*—Approximately 2 mm.

*Color.*—Upper surface: Near RHS Green 137C. Flushed Greyed-Purple 185B when immature. Lower surface: Near RHS Green 143C.

*Texture.*—Glabrous all surfaces. Small, sharp prickle present at leaflet pair attachment.

Leaflet:

*Quantity.*—3 or 5 per leaf, most commonly 3.

*Average length.*—Approximately 2.2 cm to 3.1 cm.

*Average width.*—Approximately 1.8 cm to 2.4 cm.

*Shape of blade.*—Broad ovate.

*Apex.*—Broad acute to rounded.

*Base.*—Broadly rounded.

*Margin.*—Finely serrate.

*Appearance of top surface.*—Moderately glossy.

*Appearance of bottom surface.*—Matte.

*Texture of top surface.*—Glabrous.

*Texture of bottom surface.*—Glabrous.

*Color.*—Young foliage upper side: Near RHS Yellow-Green 146C flushed Greyed-Purple 185B. Young foliage under side: Near RHS Yellow-Green 146D flushed Greyed-purple 185B. Mature foliage upper side: Near RHS Green 139A. Mature foliage under side: Near RHS Green 138A.

*Venation.*—Type: Reticulate. Venation color upper side: Near RHS Green 143C. Venation color under side: Near RHS Yellow-Green 144C.

Petiole:

*Average length.*—Approximately 1.5 cm.

*Average diameter.*—Approximately 3 mm.

*Color.*—Upper surface: Near RHS Yellow-Green 144B. Lightly flushed Greyed-Purple 185B. Lower surface: Near RHS Green 137C.

*Petiole wing.*—Typically 7 mm long and 4 mm wide. Apex apiculate. Upper surface colored near RHS Yellow-Green 144C, lower surface colored near Yellow-Green 144B.

*Texture.*—Glabrous.

FLOWER

Natural flowering season: Spring until Autumn.

Inflorescence type and habit: Average 6 single flowers arranged on terminal flower stems. Fully double rotate flowers.

Rate of flower opening: Approximately 7 days from bud to fully opened flower.
Flower longevity on plant: 5 days, after fully opened.
Quantity of flowers: 20 to 40 flowers and buds.
Flower size:
*Diameter.*—Approximately 8 cm.
*Height.*—Approximately 4.5 cm.
Flower shape:
*From above.*—Round to very slightly irregular round.
*Profile of upper part of flower.*—Convex.
*Profile of lower part of flower.*—Convex.
Peduncle:
*Length.*—2.2 cm to 2.9 cm.
*Diameter.*—3 mm.
*Color.*—Near RHS Green 143C.
*Texture.*—Glabrous.
Petals:
*Petal arrangement.*—Multiple rotate, overlapping whorls.
*Petal quantity.*—Average 35 to 40.
*Length.*—2.5 cm to 3.5 cm.
*Width.*—1.8 cm to 3.0 cm.
*Shape.*—Obovate to wide obovate.
*Margin.*—Entire. Curled moderately downward.
*Apex.*—Rounded, slightly rolled under.
*Base.*—Attenuate.
*Texture.*—Glabrous all surfaces.
*Color.*—When opening: Upper surface: Near RHS Red 52A covered in overall hue Red-Purple N57A. Large basal blotch near Yellow 13A. Lower surface: Near RHS Red 52A flushed Yellow 12A. Large basal blotch near Yellow 13A. Fully opened: Upper surface: Near RHS Red-Purple N57A flushed Red 52A. Streaked near Red 40B in center section. Large basal blotch near Yellow 13A. Lower surface: Near RHS Red 52A. Lightly streaked Yellow 12A over entire surface. Streaked near Red 40B in center section. Large basal blotch near Yellow 12A. Aging: Upper surface: Near RHS Red-Purple N57B. Center streaked near Red 43C. Margin colored near Red-Purple 61C. Large basal blotch near Yellow 12A. Lower surface: Near RHS Red-Purple 58A mixed with 58B. Irregular streaking near Red 36A. Large basal blotch near Yellow 9A.

Bud:
*Shape.*—Ovate.
*Length.*—Approximately 2.4 cm.
*Diameter.*—Approximately 1.8 cm.
*Color.*—Near RHS Red 53A. Streaks near Red-Purple N57C covering about 10% to 20%.
Sepals:
*Quantity.*—5.
*Length.*—2.2 cm.
*Width.*—7 mm.
*Shape.*—Deltoid.
*Apex.*—Apiculate. Weak sepal extensions.
*Margin.*—Entire.
*Texture.*—Pubescent upper surface, glabrous lower surface.
*Color.*—Interior Surface: Near RHS Green 138B. Exterior Surface: Near RHS Green 138A.
Receptacle:
*Height.*—11 mm.
*Width.*—11 mm.
*Shape.*—Domed.
*Color.*—Near RHS Green 138C.
Fragrance: Moderate, typical tea rose scent.

REPRODUCTIVE ORGANS

Stamens:
*Quantity.*—About 100.
*Filament length.*—Approximately 4 mm to 10 mm.
*Filament color.*—Near RHS Yellow-Orange 23A.
Anthers:
*Length.*—2 mm.
*Shape.*—Narrow globular.
*Color.*—Near RHS Orange 25B.
*Pollen.*—Color: Near RHS Orange 25B. Quantity: Moderate.
Pistil: Not observed.

OTHER CHARACTERISTICS

Seeds and fruits: Not observed.
Disease/pest resistance: Good overall disease resistance to normal pests and diseases typical of garden roses. Very good resistance to blackspot diseases.

What is claimed is:

1. A new and distinct cultivar of Floribunda Rose plant named 'LIMtropica' as herein illustrated and described.

* * * * *